United States Patent
Chen et al.

(10) Patent No.: US 10,324,076 B1
(45) Date of Patent: Jun. 18, 2019

(54) WATER QUALITY ANALYSIS INSTRUMENT

(71) Applicant: ANATEK ENTERPRISE CO., LTD., Koahsiung (TW)

(72) Inventors: Yu-Ming Chen, Koahsiung (TW); Ming-Ta Kuo, Kaohsiung (TW)

(73) Assignee: ANATEK ENTERPRISE CO., LTD., Koahsiung (TW)

( * ) Notice: Subject to any disclaimer, the term of this patent is extended or adjusted under 35 U.S.C. 154(b) by 0 days.

(21) Appl. No.: 16/161,041

(22) Filed: Oct. 15, 2018

(30) Foreign Application Priority Data

Feb. 28, 2018 (TW) .............................. 107106690 A

(51) Int. Cl.
*G01N 33/18* (2006.01)
*G01N 21/3577* (2014.01)
*G01N 1/28* (2006.01)

(52) U.S. Cl.
CPC ........... *G01N 33/1846* (2013.01); *G01N 1/28* (2013.01); *G01N 21/3577* (2013.01)

(58) Field of Classification Search
CPC ... G01N 33/1846; G01N 1/28; G01N 21/3577
USPC ........................................................ 250/343
See application file for complete search history.

(56) References Cited

U.S. PATENT DOCUMENTS

| | | | | |
|---|---|---|---|---|
| 5,275,957 A | * | 1/1994 | Blades ................... | G01N 27/06 436/133 |
| 5,661,038 A | * | 8/1997 | Brenna ................... | C01B 3/501 250/282 |
| 6,114,700 A | * | 9/2000 | Blades ............... | G01N 21/3504 250/343 |
| 6,183,695 B1 | * | 2/2001 | Godec .................... | G01N 27/06 422/76 |
| 8,420,013 B1 | * | 4/2013 | Inoue .................. | G01N 33/1846 210/143 |
| 2003/0211626 A1 | * | 11/2003 | Davenport ........... | G01N 27/021 436/146 |
| 2006/0257296 A1 | * | 11/2006 | Lipp ........................ | H05H 3/02 422/159 |
| 2011/0155272 A1 | * | 6/2011 | Conway ............. | G01N 33/1846 137/896 |
| 2011/0155912 A1 | * | 6/2011 | Conway ............. | G01N 33/1846 250/338.3 |

FOREIGN PATENT DOCUMENTS

DE 102014119547 * 2/2016 ............. G01N 21/59

* cited by examiner

*Primary Examiner* — David P Porta
*Assistant Examiner* — Gisselle M Gutierrez
(74) *Attorney, Agent, or Firm* — Chun-Ming Shih

(57) ABSTRACT

A water quality analysis instrument for performing a blowback operation and a non-volatile total organic carbon analysis operation in sequence. When the blowback operation is performed, a previous residual gas within a water sample analyzer is discharged. When the non-volatile total organic carbon analysis operation is performed, the water sample flows between an accommodating space and an UV light providing module in a circulating manner, so that the non-volatile total organic carbon in the water sample is nearly completely oxidized, so that the water sample analyzer can analyze a content of non-volatile total organic carbon in the water sample accurately.

12 Claims, 3 Drawing Sheets

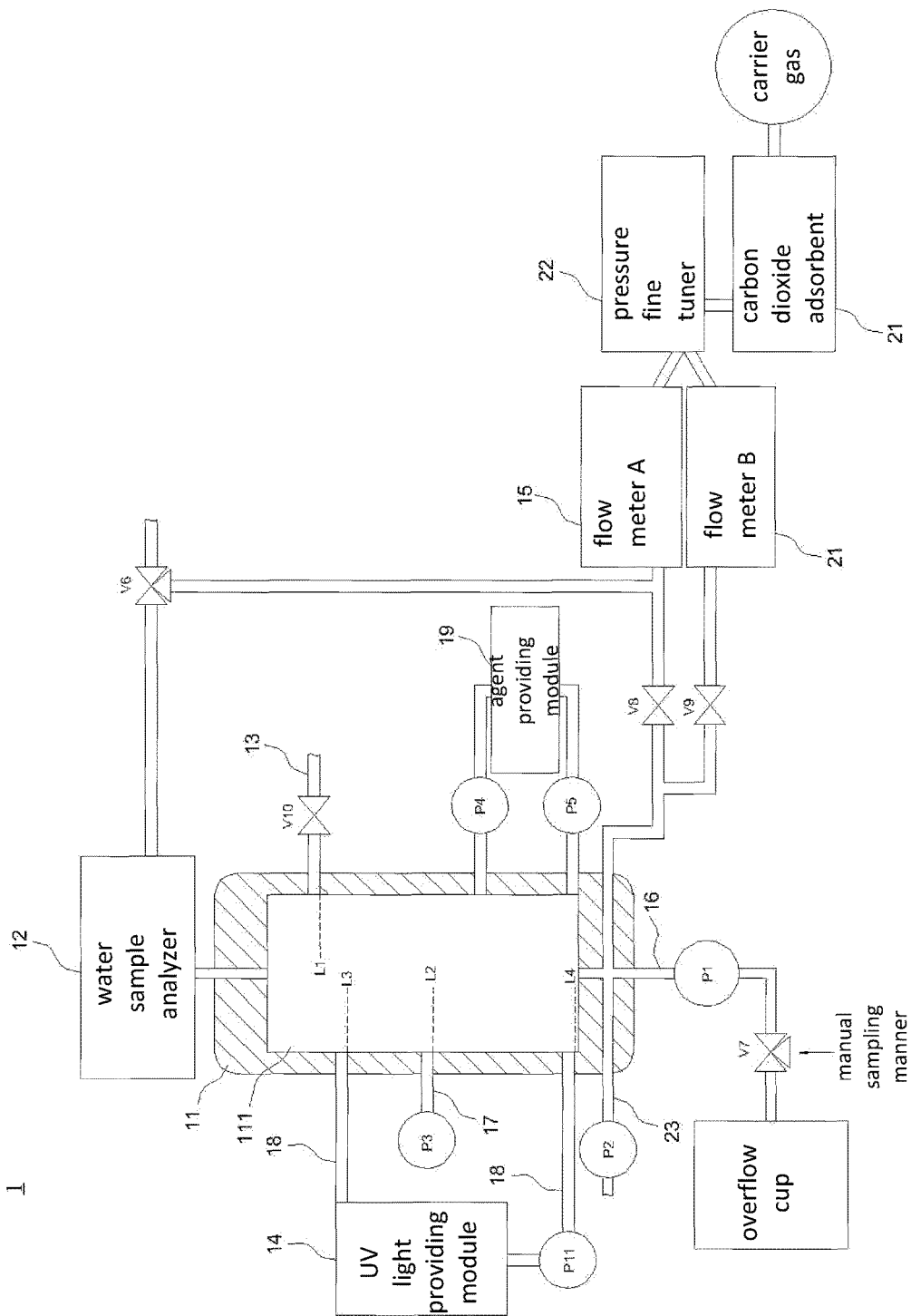
[FIG. 1]

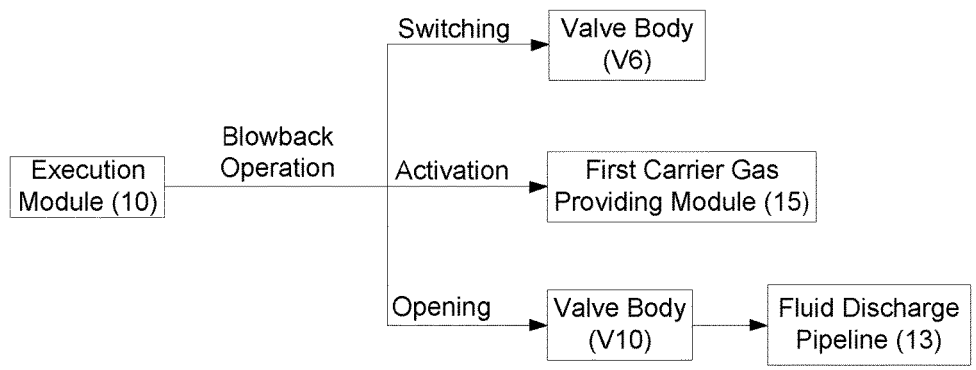
【FIG. 2A】
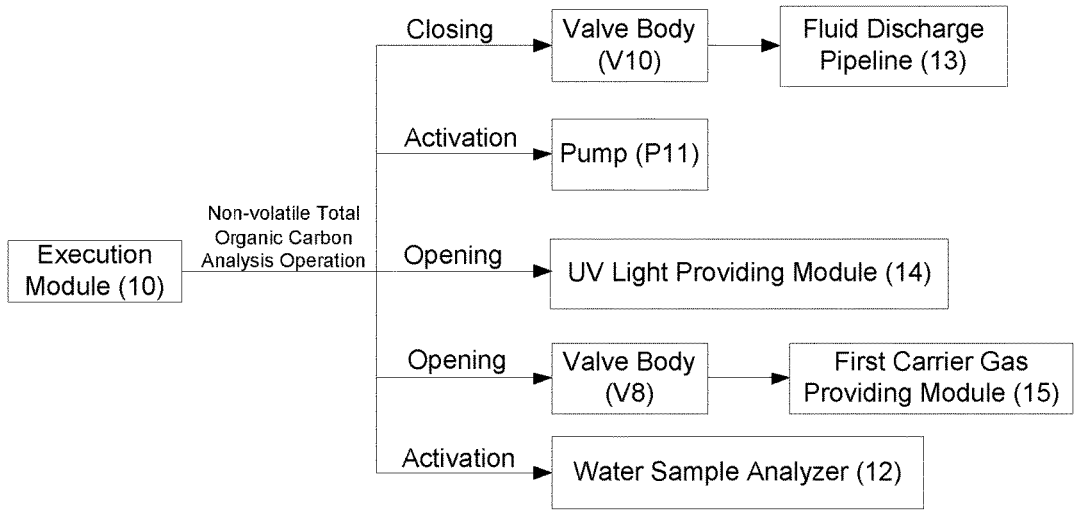
【FIG. 2B】

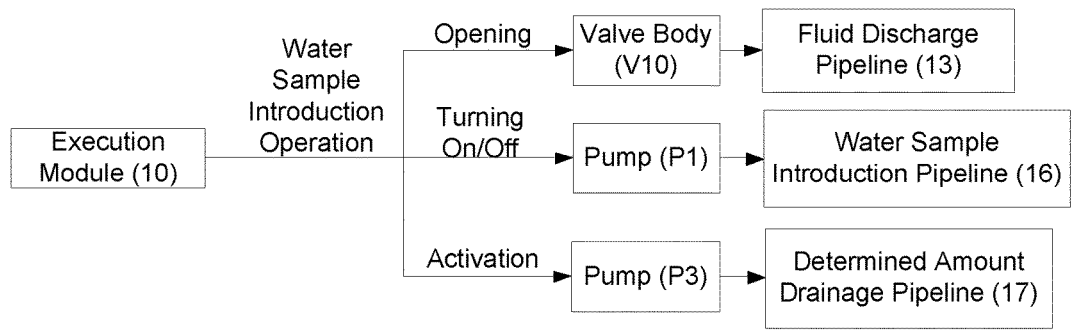
[FIG. 2C]
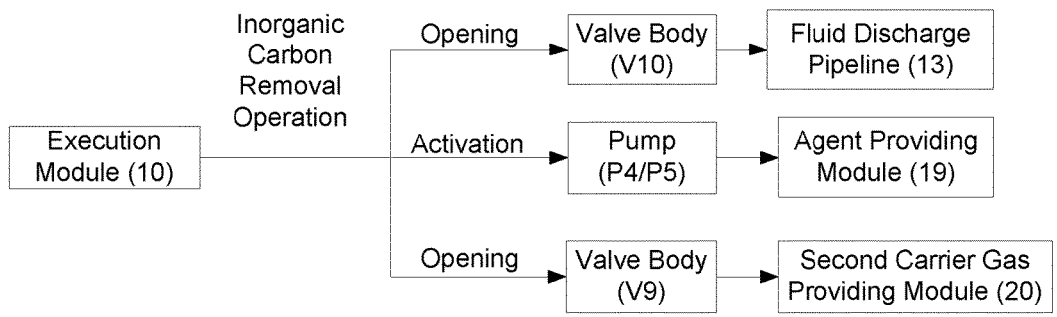
[FIG. 2D]

WATER QUALITY ANALYSIS INSTRUMENT

CROSS-REFERENCE TO RELATED APPLICATIONS

This application claims the priority of Republic of China Patent Application No. 107106690 filed on Feb. 28, 2018, in the State Intellectual Property Office of the R.O.C., the disclosure of which is incorporated herein by reference.

BACKGROUND OF THE INVENTION

Field of the Invention

The present application relates to an analysis equipment, and more particularly, to a water quality analysis instrument capable of analyzing a content of a non-volatile total organic carbon.

Descriptions of the Related Art

With attention paid to environment, various governments have regulated the content of non-volatile total organic carbon in water sample, such as sewage, to reduce environmental pollution due to the sewage. Therefore, non-volatile total organic carbon analysis equipments are widely used in the industry to analyze the content of non-volatile total organic carbon in water sample. A non-volatile total organic carbon analysis equipment typically oxidizes organic matters in a water sample, and uses a water sample analyzer, such as a non-dispersive infrared analyzer, to measure the concentration of non-volatile total organic carbon in the water sample.

However, when a gas analysis operation at one stage has been performed by a water sample analysis in a water quality analysis instrument, some gases remain in the water sample analyzer inevitably, which will be defined as previous residual gases below, and these previous residual gases will affect a gas analysis operation of the water sample analyzer at the next stage significantly, resulting in a reduced accuracy of an analysis result.

In existing technologies, there are at least three methods for oxidizing organic matters in a water sample, including: a high temperature combustion method, an UV persulfate method, and a two-stage advanced oxidation method. For the high temperature combustion method, the organic matters in the water sample are generally oxidized on the wall of a high temperature furnace, causing residual substances on the wall of the high temperature furnace, and deriving criticized issues, such as difficult cleaning. For the UV persulfate method, persulfate is generally activated by an UV light to generate hydroxyl radicals, which oxidize organic substances in a water sample. However, when the concentration of chlorine ions in the water sample exceeds 0.05%, generation of the hydroxyl radicals is inhibited, and when the turbidity of the water sample is high, the UV light may be blocked, resulting an insufficient activation of the persulfate, so that organic matters in the water sample cannot be oxidized completely, such that the analysis of a content of non-volatile total organic carbon in the water sample is inaccurate. For the two-stage advanced oxidation method, organic matters in a water sample is generally oxidized to carbon dioxide by adding an alkali agent, followed by analyzing a content of non-volatile total organic carbon in the water sample based on measurement data of carbon dioxide. However, carbon dioxide is released from the alkali agent inherently, so the use of the alkali agent, such as NaOH, will cause carbon dioxide which is not due to oxidization of the organic matters, and the analysis of the content of non-volatile total organic carbon in the water sample is inaccurate accordingly.

Therefore, the present application is intended to solve the above issues, improve an accuracy of an analysis result of a content of non-volatile total organic carbon in a water sample, and allow a smooth oxidation of the non-volatile total organic carbon in the water sample.

SUMMARY OF THE INVENTION

In view of the above drawbacks in the conventional technology, a primary object of the present invention is to provide a water quality analysis instrument, which may allow a nearly complete oxidation for non-volatile total organic carbon in the water sample, and may ensure that the water sample analyzer is not contaminated by the previous residual gas, so that the accuracy of the analysis result for the water sample may also be improved.

To achieve the above and other objects, a water quality analysis instrument for analyzing a content of a non-volatile total organic carbon in a water sample is provided in the present invention. The water quality analysis instrument comprises: an equipment body having an accommodating space therein, which accommodates the water sample; a water sample analyzer in communication with the accommodating space for analyzing the content of the non-volatile total organic carbon in the water sample within the accommodating space; a fluid discharge pipeline in communication with the accommodating space; an UV light providing module in communication with the accommodating space for providing a UV light; a first carrier gas providing module in selective communication with one of the water sample analyzer and the accommodating space for providing a first carrier gas; and an execution module sequentially performing a blowback operation and a non-volatile total organic carbon analysis operation; wherein when the execution module performs the blowback operation, the fluid discharge pipeline is opened, and the first carrier gas providing module is in communication with the water sample analyzer for providing the first carrier gas to the water sample analyzer, such that a previous residual gas in the water sample analyzer enters the accommodating space along with the first carrier gas, and then is discharged out of the accommodating space through the fluid discharge pipeline; when the execution module performs the non-volatile total organic carbon analysis operation, the fluid discharge pipeline is closed for the water sample to flow between the accommodating space and the UV light providing module in a circulating manner, in order to provide the UV light for the water sample flowing through the UV light providing module, so that the non-volatile total organic carbon in the water sample is oxidized to generate a non-volatile total organic carbon gaseous oxide, followed by causing the first carrier gas providing module to provide the accommodating space with the first carrier gas for forcing a release of the non-volatile total organic carbon gaseous oxide in the water sample into the water sample analyzer, as well as analyzing the content of the non-volatile total organic carbon in the water sample within the accommodating space.

Alternatively, the water quality analysis instrument said above, wherein the non-volatile total organic carbon gaseous oxide is a carbon dioxide.

Alternatively, the water quality analysis instrument said above further comprises a carbon dioxide adsorbent located in the first carrier gas providing module to adsorb a carbon dioxide in the first carrier gas.

Alternatively, the water quality analysis instrument said above, wherein the water sample analyzer is a non-dispersive infrared analyzer.

Alternatively, the water quality analysis instrument said above, wherein the UV light has a light wavelength between 100 and 200 nm and/or between 200 and 280 nm.

Alternatively, the water quality analysis instrument said above, wherein the accommodating space has an overflow water level and a determined amount water level, the overflow water level being higher than the determined amount water level, and the fluid discharge pipeline is extended from the overflow water level of the accommodating space to outside of the equipment body, the water quality analysis instrument further comprising: a water sample introduction pipeline in communication with a bottom of the accommodating space; and a determined amount drainage pipeline in communication with the accommodating space, extending from the determined amount water level of the accommodating space to the outside of the equipment body; wherein the execution module further performs a water sample introduction operation, in which the fluid discharge pipeline is opened when the execution module performs the water sample introduction operation, causing the water sample introduction pipeline to activate an introduction for the water sample to be introduced from the bottom of the accommodating space into the accommodating space, and causing the water sample in the accommodating space beyond the overflow water level to be discharged through the fluid discharge pipeline, so that the water level of the water sample in the accommodating space is at the overflow water level, followed by closing the water sample introduction pipeline and opening the determined amount drainage pipeline for the water sample in the accommodating space beyond the determined amount water level to be discharged through the determined amount drainage pipeline, such that the water sample in the accommodating space has a water level at the determined amount water level, allowing the accommodating space to accommodate a determined amount of the water sample.

Alternatively, the water quality analysis instrument said above, wherein the accommodating space has a circulating high water level and a circulating low water level, the water quality analysis instrument further comprising: a water sample circulation pipeline in communication with the accommodating space, and extending from the circulating low water level to the circulating high water level via the UV light providing module; when the execution module performs the non-volatile total organic carbon analysis operation, the water sample circulation pipeline drives the water sample in the accommodating space to flow from the circulating low water level to the circulating high water level via the UV light providing module and enter the accommodating space again, such that a flow of the water sample between the accommodating space and the UV light providing module in a circulating manner is realized.

Alternatively, the water quality analysis instrument said above, wherein the circulating high water level is higher than the determined amount water level, and the circulating low water level is lower than the determined amount water level.

Alternatively, the water quality analysis instrument said above, wherein the circulating high water level is between the overflow water level and the determined amount water level, and the circulating low water level is at the bottom of the accommodating space.

Alternatively, the water quality analysis instrument said above, further comprises: an agent providing module in communication with the accommodating space for providing an agent; and a second carrier gas providing module in selective communication with the accommodating space for providing a second carrier gas; wherein the execution module further performs an inorganic carbon removal operation; when the execution module performs the inorganic carbon removal operation, the fluid discharge pipeline is opened, causing the agent providing module to provide the water sample within the accommodating space with the agent for acidifying the water sample, such that an inorganic carbon in the water sample is converted into a carbon dioxide, followed by causing the second carrier gas providing module to provide the accommodating space with the second carrier gas, forcing the carbon dioxide in the water sample to be released and discharged through the fluid discharge pipeline.

Alternatively, the water quality analysis instrument said above, wherein the first carrier gas providing module and the second carrier gas providing module are respectively flow meters, the first carrier gas providing module providing the first carrier gas having a first flow rate, the second carrier gas providing module providing the second carrier gas having a second flow rate, wherein the first flow rate is less than the second flow rate, the first flow rate being defined by a tolerable carrier gas flow rate of the water sample analyzer, the second flow rate being defined by the carrier gas flow rate capable of forcing the carbon dioxide in the water sample to be released.

Alternatively, the water quality analysis instrument said above, wherein when the execution module performs the inorganic carbon removal operation, the UV light providing module keeps on providing the UV light, and closes the water sample circulation pipeline, so that the water sample in the accommodating space is not affected by the UV light when the execution module performs the inorganic carbon removal operation.

In comparison to prior arts, the water quality analysis instrument according to the present application, at first, a blowback operation is performed to provide a first carrier gas in a manner such that a previous residual gas within a water sample analyzer may be discharged along with the first carrier gas to ensure that the water sample analyzer is not contaminated by the previous residual gas, and then a non-volatile total organic carbon analysis operation is performed for the water sample to flow between an accommodating space and an UV light providing module in a circulating manner, allowing a nearly complete oxidation for non-volatile total organic carbon in the water sample. Therefore, the present application may solve the issues in prior arts that the water sample analyzer is susceptible to contamination by the previous residual gas, and the non-volatile total organic carbon in the water sample cannot be oxidized successfully, thereby improving the water sample analyzer effectively with respect to an accuracy of an analysis result for a content of the non-volatile total organic carbon in the water sample.

BRIEF DESCRIPTION OF THE DRAWINGS

The above and other aspects, features and other advantages of the present invention will be more clearly understood from the following detailed description taken in conjunction with the accompanying drawings, in which:

FIG. 1 is a schematic diagram showing an overall structure for an embodiment of a water quality analysis instrument according to the present application.

FIG. 2A is a schematic diagram showing a control for an execution module when a water quality analysis instrument performs a blowback operation according to the present application.

FIG. 2B is a schematic diagram showing a control for an execution module when a water quality analysis instrument performs a non-volatile total organic carbon analysis operation according to the present application.

FIG. 2C is a schematic diagram showing a control for an execution module when a water quality analysis instrument performs a water sample introduction operation according to the present application.

FIG. 2D is a schematic diagram showing a control for an execution module when a water quality analysis instrument performs an inorganic carbon removal operation according to the present application.

DETAILED DESCRIPTION OF THE PREFERRED EMBODIMENT

Embodiments of the present invention will now be described in detail with reference to the accompanying drawings. The present invention may, however, be embodied in many different forms and should not be construed as being limited to the embodiments set forth herein. Rather, these embodiments are provided so that this disclosure will be thorough and complete, and will fully convey the scope of the present invention to those skilled in the art. In the drawings, the shapes and dimensions of elements may be exaggerated for clarity, and the same reference numerals will be used throughout to designate the same or like components.

In the present application, a water quality analysis instrument is provided for analyzing a content (concentration) of non-volatile total organic carbon in a water sample. The technical idea of the present application is described below with reference to FIG. 1, FIG. 2A to FIG. 2D.

As shown in FIG. 1, a water quality analysis instrument 1 according to the present application includes an equipment body 11, a water sample analyzer 12, a fluid discharge pipeline 13, an UV light providing module 14 and a first carrier gas providing module 15.

The equipment body 11 has an accommodating space 111 therein for accommodating a determined amount of a water sample.

The water sample analyzer 12 is, for example, a non-dispersive infrared analyzer in communication with the accommodating space 111 for analyzing a content of non-volatile total organic carbon of the water sample within the accommodating space 111.

The fluid discharge pipeline 13 is in communication with the accommodating space 111 for discharging a gas, such as carbon dioxide, or a liquid, such as a water sample, within the accommodating space 111. The fluid discharge pipeline 13 is provided with a valve body V10 for controlling opening and closing of the fluid discharge pipeline 13.

The accommodating space 111 has an overflow water level L1 and a determined amount water level L2 therein, the overflow water level L1 being higher than the determined amount water level L2. The water quality analysis instrument 1 further includes a water sample introduction pipeline 16 and a determined amount drainage pipeline 17. As shown in FIG. 1, the water sample introduction pipeline 16 is provided with a pump P1 and communicated with a bottom of the accommodating space 111 for the water sample to enter the accommodating space 111 from bottom to top by activating the pump P1. A front end of the water sample introduction pipeline 16 is provided with a valve body V7, such as a three-way valve, for the water sample introduction pipeline 16 to opt to introduce the water sample from an overflow cup which is kept in communication with a remote sampling source, or introduce the water sample in a manual sampling manner.

The fluid discharge pipeline 13 is extended from the overflow water level L1 of the accommodating space 111 to outside of the equipment body 11, and the valve body V10 is opened to discharge the water sample within the accommodating space 111 beyond the overflow water level L1 via the fluid discharge pipeline 13, such that the highest water level of the water sample within the accommodating space 111 is at the overflow water level L1, thereby avoiding excessive water sample within the accommodating space 111.

The determined amount drainage pipeline 17 is provided with a pump P3 and is communicated with the accommodating space, and is extended from the determined amount water level L2 of the accommodating space 111 to the outside of the equipment body 11, and the pump P3 is activated to discharge the water sample within the accommodating space 111 beyond the determined amount water level L2 for the water sample to be analyzed within the accommodating space 111 to be at the determined amount water level L2, such that a determined amount of the water sample is accommodated in the accommodating space 111, thereby allowing an analysis condition for the water sample to meet expectation.

The water quality analysis instrument 1 may further include a bottom drainage pipeline 23, which is provided with a pump P2 and extended from the bottom of the accommodating space 111 to the outside of the equipment body 11, and the water sample within the accommodating space 111 is completely discharged via the bottom drainage pipeline 23 by an activation of the pump P2.

The UV light providing module 14 is in communication with the accommodating space 111 for providing a water sample flowing through the UV light providing module 14 with an UV light having a wavelength of between 100 and 200 nm and/or between 200 and 280 nm to oxidize non-volatile total organic carbon in the water sample, resulting in a non-volatile total organic carbon gaseous oxide, such as carbon dioxide.

Specifically, when there is interference of chlorine ions in the water sample, the UV light providing module 14 may provide the water sample with an UV light having a wavelength between 100 and 200 nm, and allow oxygen provided by the first carrier gas providing module 15 to react for generation of ozone, which removes the chlorine ions in the water sample to solve the issues with respect to salt interference and low water sample measurement.

The UV light providing module 14 may also provide the water sample with an UV light having a wavelength between 200 and 280 nm, and allow oxygen to react with the water sample for generation of hydroxyl radicals by irradiation of light and catalysis of catalyst, resulting in an accurate analysis for a content of the non-volatile total organic carbon in the water sample using organic matters in the water sample oxidized by the generated hydroxyl radicals.

Alternatively, the UV light providing module 14 may be constructed of two UV light providing equipments to provide the water sample with an UV light having a wavelength between 100 and 200 nm and a UV light having a wavelength between 200 and 280 nm, respectively.

As shown in FIG. 1, the water quality analysis instrument 1 further has a water sample circulation pipeline 18, and correspondingly, the accommodating space 111 is provided with a circulating high water level L3 and a circulating low water level L4 therein. The water sample circulation pipeline 18 is provided with a circulating pump P11 and communicated with the accommodating space 111 of the equipment body 11, and is extended from the circulating low water level L4 of the accommodating space 111 to the circulating high water level L3 of the accommodating space 111 via the UV light providing module 14. The water sample circulation pipeline 18 may utilize activation of the circulating pump P11 for the water sample in the accommodating space 111 to flow from the circulating low water level L4 to the circulating high water level L3 via the UV light providing module 14, followed by flowing back into the accommodating space 111, thereby realizing a circulating flow effect between the accommodating space 111 and the UV light providing module 14 for the water sample.

As shown in FIG. 1, the circulating high water level L3 is between the overflow water level L1 and the determined amount water level L2, while the circulating low water level L4 is at the bottom of the accommodating space 111. Since the circulating high water level L3 is higher than the determined amount water level L2, and the circulating low water level L4 is lower than the determined amount water level L2, the water sample will fall from the circulating high water level L3 to the determined amount water level L2 during the circulation process, so that sufficient disturbance of the water sample is helpful for release of non-volatile total organic carbon gaseous oxides from the water sample.

Alternatively, the UV light providing module 14 is provided outside the accommodating space 111 separately. As such, even if the water quality analysis instrument 1 is performing related operations other than the non-volatile total organic carbon analysis operation, such as performing a leading inorganic carbon removal operation, the UV light providing module 14 may be always in an on state by closing the water sample circulation pipeline 18, so that the water sample within the accommodating space 111 is not affected by the UV light even though the UV light providing module 14 is switched on during the inorganic carbon removal operation, in order to prevent the non-volatile total organic carbon in the water sample from oxidization in an inappropriate occasion. Thus, unnecessary waiting time due to repetitive switching on and off of the UV light providing module 14 may be saved (waiting for a period of time is required for the UV light providing module 14 to perform a normal light oxidation operation after switching on) to improve the execution efficiency of the analysis operation.

The first carrier gas providing module 15 may be in selective communication with the water sample analyzer 12 or the accommodating space 111 to provide a first carrier gas, such as oxygen or nitrogen. Based on the improvement of the reaction efficiency, using oxygen as the first carrier gas is preferred.

As shown in FIG. 1, the first carrier gas providing module 15 and a transmission passage of the water sample analyzer 12 are provided with a valve body V6, such as a three-way valve, therebetween, through which the water sample analyzer 12 may be allowed to communicate with the first carrier gas providing module 15 or an external environment selectively. After the valve body V6 is switched such that the first carrier gas providing module 15 is in communication with the water sample analyzer 12 and the valve body V8 is closed, the first carrier gas providing module may provide the water sample analyzer with the first carrier gas. After the valve body V6 is switched such that a passage between the first carrier gas providing module 15 and the water sample analyzer 12 is disconnected, the water sample analyzer 12 may communicate with an external environment via the valve body V6 to discharge an analytical gas within the water sample analyzer 12. After the valve body V8 is opened, the first carrier gas providing module 15 is communicated with the accommodating space 111 for the first carrier gas to be provided to the accommodating space 111.

Furthermore, the water quality analysis instrument 1 according to the present application is further provided with an agent providing module 19 and a second carrier gas providing module 20.

The agent providing module 19 is in communication with the accommodating space 111, such that an agent containing oxidant and acid agent is pumped into the accommodating space 111 by a pump P4 and a pump P5 to be mixed with the water sample for performing the inorganic carbon removal operation.

The second carrier gas providing module 20 may communicate with the accommodating space 111 through the opening and closing of the valve body V9 selectively to connect or disconnect the transmission passage between the second carrier gas providing module 20 and the accommodating space 111, such that the second carrier gas is provided to the accommodating space 111 duly.

The first carrier gas providing module 15 may be a flow meter A for providing a first carrier gas having a first flow rate, and the second carrier gas providing module 20 may be a flow meter B for providing a second carrier gas having a second flow rate. The magnitude of the first flow rate is defined by a tolerable carrier gas flow rate of the water sample analyzer 12, and the magnitude of the second flow rate is defined by a carrier gas flow rate capable of releasing carbon dioxide from the water sample. For example, the magnitude of the flow rate of the flow meter A is designed to be 200 cc/min, and that of the flow rate of the flow meter B is designed to be 400 cc/min, so that the first flow rate is smaller than the second flow rate.

The first and second carrier gas providing modules 15 and 20 are disposed independently and may adjust flow rates separately. For example, the first carrier gas providing module 15 may maintain a constant magnitude of the flow rate to meet the tolerable carrier gas flow rate of the water sample analyzer 12. Nevertheless, since actual concentrations (contents) of inorganic carbon in different water samples may be different, the second carrier gas providing module 20 may adjust the magnitude of the flow rate in response to the actual concentration of inorganic carbon in the water sample. As the actual concentration of inorganic carbon in the water sample is higher, the flow rate of the second carrier gas providing module 20 is increased. As the actual concentration of inorganic carbon in the water sample is lower, the flow rate of the second carrier gas providing module 20 is decreased. Thereby, the efficiency for removal of inorganic carbon from the water sample is improved. However, the first and second carrier gas providing modules according to the present application may also be designed as a single equipment to meet the requirement of equipment simplification.

In the present application, the water quality analysis instrument 1 may further have carbon dioxide adsorbents 21, such as zeolite, provided in the first and second carrier gas providing modules 15 and 20 for adsorbing carbon dioxide in the first and second carrier gases, to reduce the contents of carbon dioxide in the first and second carrier gases, and prevent the carbon dioxide in the first and second carrier gases from affecting an analysis result of water quality. Moreover, in order to prevent the first and second carrier gas providing modules 15 and 20 from being impacted by a high pressure carrier gas to affect a service life thereof, pressure fine tuners 22 may be disposed at the front ends of the first and second carrier gas providing modules, to fine tune the input pressure of the carrier gas.

Based on the composition structure mentioned above, the water quality analysis instrument 1 according to the present application further has an execution module 10 for controlling operation execution of various components mentioned above to perform water quality analysis related operations, which will be described specifically below with reference to FIG. 2A to FIG. 2D:

As shown in FIG. 2A and FIG. 1, as the execution module 10 performs a blowback (also referred to as backflush) operation, the valve body V10 is opened to open the fluid discharge pipeline 13, and the valve body V6 is switched for the first carrier gas providing module 15 to be in communication with the water sample analyzer 12, while the valve body V8 is closed, and the first carrier gas providing module 15 is activated for providing the water sample analyzer 12 with the first carrier gas having the positive pressure airflow, such that the previous residual gas within the water sample analyzer 12 enters the accommodating space 111 along with the first carrier gas reversely, and is discharged from the accommodating space 111 via the opened fluid discharge pipeline 13, thereby preventing the water sample analyzer 12 from having the previous residual gas, which resulting in inaccurate subsequent analysis results.

As shown in FIG. 2B and FIG. 1, as the execution module 10 performs the non-volatile total organic carbon analysis operation, the valve body V10 is closed to close the passage of the fluid discharge pipeline 13, followed by activating the pump P11 and turning on the UV light providing module 14 and the water sample analyzer 12 for the water sample to flow between the accommodating space 111 and the UV light providing module 14 in a circulating manner, such that an UV light is provided to the water sample flowing through the UV light providing module 14 to thereby oxidize the non-volatile total organic carbon in the water sample for generation of a non-volatile total organic carbon gaseous oxide, and then the execution module 10 opens the valve body V8 and switches the valve body V6 to disconnect the passage between the first carrier gas providing module 15 and the water sample analyzer 12, causing the first carrier gas providing module 15 to provide the accommodating space 111 with the first carrier gas, forcing the non-volatile total organic carbon gaseous oxide in the water sample to be released into the water sample analyzer 12 to analyze the content of the non-volatile total organic carbon in the water sample within the accommodating space 111.

As the pump P11 is turned on, the water sample circulation pipeline 18 drives the water sample of the accommodating space 111 into the UV light providing module 14 from the circulating low water level L4 to oxidize the non-volatile total organic carbon in the water sample by irradiation of an UV light, such that a non-volatile total organic carbon gaseous oxide, such as carbon dioxide, is generated. The oxidized water sample will flow to the circulating high water level L3 via the water sample circulation pipeline 18, and enter the accommodating space 111 again to realize a flow of the water sample between the accommodating space 111 and the UV light providing module 14 in a circulating manner, so that a smooth oxidization of the water sample of the accommodating space 111 is ensured. Since the water level of the water sample accommodated within the accommodating space 111 is at the determined amount water level L2, and the circulating high water level L3 is higher than the determined amount water level L2, as the water sample returns into the accommodating space via the circulating high water level L3 again, a process of falling from top to bottom will be undergone, which is helpful for release of the non-volatile total organic carbon gaseous oxide generated in the water sample.

In the present application, the non-volatile total organic carbon analysis operation is performed after the blowback operation, in order for the previous residual gas remaining therein to be removed before the water sample analyzer performs the non-volatile total organic carbon analysis operation, thereby improving the accuracy of analysis result.

As shown in FIG. 2C and FIG. 1, as the execution module 10 performs the water sample introduction operation, the valve body V10 is opened to open the fluid discharge pipeline 13, followed by activating the pump P1 for the water sample introduction pipeline 16 to activate introduction, such that the water sample is introduced into the accommodating space 111 from the bottom of the accommodating space 111. During the introduction process, the water sample beyond the overflow water level L1 in the accommodating space 111 may be discharged by the opened fluid discharge pipeline 13 for the water level of the water sample in the accommodating space 111 to be at the overflow water level L1. Moreover, after the water level of the water sample reaches the overflow water level L1, the execution module 10 turns off the pump P1, causing the water sample introduction pipeline 16 to stop introduction of the water sample, and the pump P3 is turned on to discharge the water sample beyond the determined amount water level L2 in the accommodating space 111 by the determined amount drainage pipeline 17, such that the water level of water sample within the accommodating space 111 is at a determined amount water level L2, so as to achieve the purpose of accommodating a determined amount of the water sample in the accommodating space 111, allowing an analysis condition for the water sample to meet expectation. As the execution module 10 is performing the water sample introduction operation, the blowback operation mentioned above may also be performed simultaneously to provide the water sample analyzer 12 with the first carrier gas having a positive pressure, in order to prevent the moisture generated in the water sample from entering the water sample analyzer 12 during the process of performing the water sample introduction operation, such that the water sample analyzer 12 is kept dry.

As shown in FIG. 2D and FIG. 1, as the execution module 10 performs the inorganic carbon removal operation, the valve body V10 is opened to open the fluid discharge pipeline 13, followed by activating the pumps P4 and P5 for the agent providing module 19 to provide the water sample within the accommodating space 111 with an agent, which is used for acidifying the water sample within the accommodating space 111 to convert inorganic carbon in the water sample into carbon dioxide, and then the execution module 10 opens the valve body V9, causing the second carrier gas providing module 20 to provide the accommodating space 111 with the second carrier gas for forcing the carbon dioxide generated in the water sample to be released and discharged via the fluid discharge pipeline 13.

The inorganic carbon discharge operation mentioned above may be performed after the water sample introduction operation and before the non-volatile total organic carbon analysis operation. Moreover, in performing the inorganic carbon removal operation, the blowback operation may also be performed simultaneously for blowing out the first carrier to the accommodating space via the water sample analyzer reversely, and the carbon dioxide released from the water sample is taken away and discharged via the fluid discharge pipeline quickly.

In summary, the water quality analysis instrument according to the present application performs a blowback operation before a non-volatile total organic carbon analysis operation, and provides the water sample analyzer with a carrier gas having a positive pressure for a previous residual gas within the water sample analyzer to be discharged, so that an analysis result of the water sample analysis is accurate. Furthermore, in performing the non-volatile total organic carbon analysis operation, the present application allows a nearly complete oxidation for the non-volatile total organic carbon in the water sample by causing the water sample to flow between the accommodating space and the UV light providing module in a circulating manner, so that the accuracy of the analysis result for the water sample may also be improved.

The examples above are only illustrative to explain principles and effects of the present invention, but not to limit the present invention. It will be apparent to those skilled in the art that modifications and variations can be made without departing from the spirit and scope of the present invention. Therefore, the protection range of the rights of the present invention should be as defined by the appended claims.

What is claimed is:

1. A water quality analysis instrument for analyzing a content of a non-volatile total organic carbon in a water sample, comprising:
    an equipment body having an accommodating space therein, which accommodates the water sample;
    a water sample analyzer in communication with the accommodating space for analyzing the content of the non-volatile total organic carbon in the water sample within the accommodating space;
    a fluid discharge pipeline in communication with the accommodating space;
    an UV light providing module in communication with the accommodating space for providing a UV light;
    a first carrier gas providing module in selective communication with one of the water sample analyzer and the accommodating space for providing a first carrier gas; and
    an execution module sequentially performing a blowback operation and a non-volatile total organic carbon analysis operation; wherein
    when the execution module performs the blowback operation, the fluid discharge pipeline is opened, and the first carrier gas providing module is in communication with the water sample analyzer for providing the first carrier gas to the water sample analyzer, such that a previous residual gas in the water sample analyzer enters the accommodating space along with the first carrier gas, and then is discharged out of the accommodating space through the fluid discharge pipeline;
    when the execution module performs the non-volatile total organic carbon analysis operation, the fluid discharge pipeline is closed for the water sample to flow between the accommodating space and the UV light providing module in a circulating manner, in order to provide the UV light for the water sample flowing through the UV light providing module, so that the non-volatile total organic carbon in the water sample is oxidized to generate a non-volatile total organic carbon gaseous oxide, followed by causing the first carrier gas providing module to provide the accommodating space with the first carrier gas for forcing a release of the non-volatile total organic carbon gaseous oxide in the water sample into the water sample analyzer, as well as analyzing the content of the non-volatile total organic carbon in the water sample within the accommodating space.

2. The water quality analysis instrument according to claim 1, wherein the non-volatile total organic carbon gaseous oxide is a carbon dioxide.

3. The water quality analysis instrument according to claim 1, further comprising a carbon dioxide adsorbent located in the first carrier gas providing module to adsorb a carbon dioxide in the first carrier gas.

4. The water quality analysis instrument according to claim 1, wherein the water sample analyzer is a non-dispersive infrared analyzer.

5. The water quality analysis instrument according to claim 1, wherein the UV light has a light wavelength between 100 and 200 nm and/or between 200 and 280 nm.

6. The water quality analysis instrument according to claim 1, wherein the accommodating space has an overflow water level and a determined amount water level, the overflow water level being higher than the determined amount water level, and the fluid discharge pipeline is extended from the overflow water level of the accommodating space to outside of the equipment body, the water quality analysis instrument further comprising:
    a water sample introduction pipeline in communication with a bottom of the accommodating space; and
    a determined amount drainage pipeline in communication with the accommodating space, extending from the determined amount water level of the accommodating space to the outside of the equipment body; wherein
    the execution module further performs a water sample introduction operation, in which the fluid discharge pipeline is opened when the execution module performs the water sample introduction operation, causing the water sample introduction pipeline to activate an introduction for the water sample to be introduced from the bottom of the accommodating space into the accommodating space, and causing the water sample in the accommodating space beyond the overflow water level to be discharged through the fluid discharge pipeline, so that the water level of the water sample in the accommodating space is at the overflow water level, followed by closing the water sample introduction pipeline and opening the determined amount drainage pipeline for the water sample in the accommodating space beyond the determined amount water level to be discharged through the determined amount drainage pipeline, such that the water sample in the accommodating space has a water level at the determined amount water level, allowing the accommodating space to accommodate a determined amount of the water sample.

7. The water quality analysis instrument according to claim 6, wherein the accommodating space has a circulating high water level and a circulating low water level, the water quality analysis instrument further comprising:
    a water sample circulation pipeline in communication with the accommodating space, and extending from the circulating low water level to the circulating high water level via the UV light providing module;
    when the execution module performs the non-volatile total organic carbon analysis operation, the water sample circulation pipeline drives the water sample in the accommodating space to flow from the circulating low water level to the circulating high water level via the UV light providing module and enter the accommodating space again, such that a flow of the water sample between the accommodating space and the UV light providing module in a circulating manner is realized.

8. The water quality analysis instrument according to claim 7, wherein the circulating high water level is higher than the determined amount water level, and the circulating low water level is lower than the determined amount water level.

9. The water quality analysis instrument according to claim 8, wherein the circulating high water level is between the overflow water level and the determined amount water level, and the circulating low water level is at the bottom of the accommodating space.

10. The water quality analysis instrument according to claim 1, further comprising:
an agent providing module in communication with the accommodating space for providing an agent; and
a second carrier gas providing module in selective communication with the accommodating space for providing a second carrier gas; wherein
the execution module further performs an inorganic carbon removal operation;
when the execution module performs the inorganic carbon removal operation, the fluid discharge pipeline is opened, causing the agent providing module to provide the water sample within the accommodating space with the agent for acidifying the water sample, such that an inorganic carbon in the water sample is converted into a carbon dioxide, followed by causing the second carrier gas providing module to provide the accommodating space with the second carrier gas, forcing the carbon dioxide in the water sample to be released and discharged through the fluid discharge pipeline.

11. The water quality analysis instrument according to claim 10, wherein the first carrier gas providing module and the second carrier gas providing module are respectively flow meters, the first carrier gas providing module providing the first carrier gas having a first flow rate, the second carrier gas providing module providing the second carrier gas having a second flow rate, wherein the first flow rate is less than the second flow rate, the first flow rate being defined by a tolerable carrier gas flow rate of the water sample analyzer, the second flow rate being defined by the carrier gas flow rate capable of forcing the carbon dioxide in the water sample to be released.

12. The water quality analysis instrument according to claim 10, wherein when the execution module performs the inorganic carbon removal operation, the UV light providing module keeps on providing the UV light, and closes the water sample circulation pipeline, so that the water sample in the accommodating space is not affected by the UV light when the execution module performs the inorganic carbon removal operation.

* * * * *